United States Patent [19]
McDonell et al.

[11] Patent Number: 4,783,340
[45] Date of Patent: Nov. 8, 1988

[54] TWO-PACKAGE CO-SPRAYABLE FILM-FORMING SANITIZER

[75] Inventors: James A. McDonell, St. Paul; Richard B. Greenwald, Eagan, both of Minn.

[73] Assignee: Ecolab Inc., St. Paul, Minn.

[21] Appl. No.: 43,948

[22] Filed: Apr. 29, 1987

[51] Int. Cl.$^4$ .......................... B05D 5/00; B05D 1/02
[52] U.S. Cl. .......................................... 427/2; 427/426; 424/166; 424/405
[58] Field of Search ................ 424/405, 166; 427/426, 427/385.5, 2

[56] References Cited

U.S. PATENT DOCUMENTS

| | | | |
|---|---|---|---|
| 2,931,753 | 4/1960 | Chesbro et al. | 167/22 |
| 2,984,639 | 5/1961 | Stamberger et al. | 260/32.4 |
| 3,325,402 | 6/1967 | Erskine | 210/64 |
| 3,328,409 | 6/1967 | Wakeman et al. | 260/286 |
| 3,560,507 | 2/1971 | Wakeman et al. | 260/286 |
| 3,576,760 | 4/1971 | Gould et al. | 252/403 |
| 3,590,118 | 6/1971 | Conrady et al. | 424/405 |
| 3,886,125 | 5/1975 | Chromecek | 260/78.3 |
| 3,966,902 | 6/1976 | Chromecek | 424/59 |
| 4,013,696 | 3/1977 | Babbitt et al. | 428/412 |
| 4,132,686 | 1/1979 | Toyoshima et al. | 427/426 X |
| 4,193,993 | 3/1980 | Hilditch | 424/166 X |
| 4,199,564 | 4/1980 | Silver et al. | 424/80 |
| 4,210,161 | 7/1980 | Wagman | 132/7 |
| 4,340,522 | 7/1982 | Bronstein-Bonte et al. | 524/766 |
| 4,416,297 | 11/1983 | Wolfram et al. | 132/7 |
| 4,479,840 | 10/1984 | Takegawa et al. | 427/426 X |
| 4,500,339 | 2/1985 | Young et al. | 427/2 |
| 4,517,351 | 5/1985 | Szymanski et al. | 527/312 |

FOREIGN PATENT DOCUMENTS 54-97631 8/1979 Japan .................................. 427/426
2108866A 5/1983 United Kingdom .

OTHER PUBLICATIONS vol. 24, pp. 381–383, 431–433 of the Kirk-Othmer Encyclopedia of Chemical Technology, Third Edition.
pp. 524–525 of the Kirk-Othmer Encyclopedia of Chemical Technology, Third Edition.
vol. 19, pp. 521–531 of the Kirk-Othmer Encyclopedia of Chemical Technology, Third Edition.
vol. 13, pp. 233–235 of the Kirl-Othmer Encyclopedia of Chemical Technology, Third Edition.
vol. 7, pp. 815–819 of the Kirk-Othmer Encyclopedia of Chemical Technology, Third Edition.
vol. 3, pp. 172–175 of the Kirk-Othmer Encyclopedia of Chemical Technology, Third Edition.
vol. 10, pp. 501–504 of the Kirk-Othmer Encyclopedia of Chemical Technology, Third Edition.

Primary Examiner—Shrive Beck
Attorney, Agent, or Firm—Merchant, Gould, Smith, Welter & Schmidt

[57] ABSTRACT

A uniform, continuous sanitizing film can be formed by simultaneously spraying a two-package aqueous sanitizing composition comprising in a first solution a quaternary ammonium salt compound and in a second solution a polymer containing acid functionality. The sprays are directed to areas of substantial overlap resulting in a reaction between the quaternary ammonium compound and the carboxylic acid functional polymeric compound resulting in formation of a water insoluble film.

20 Claims, No Drawings

TWO-PACKAGE CO-SPRAYABLE FILM-FORMING SANITIZER

FIELD OF THE INVENTION

The invention relates to compositions providing sanitization or antimicrobial action on typically hard surfaces by forming a substantially water resistant film that contains compositions providing a substantial sanitizing kill of microorganisms. More particularly, the invention relates to compositions and methods used to form films of an insoluble reaction product of a quaternary ammonium compound and a carboxylic acid, sulfonic acid, or phosphonic acid functional polymer.

BACKGROUND OF THE INVENTION

A great deal of attention has been focused in recent years on sanitizing the surfaces of areas where the growth of microbial populations can pose a serious hazard to human health. Such areas can include hospitals, food preparation installations, food manufacturing areas, biological substance manufacturing areas, and others. The surfaces requiring sanitization can be treated with a variety of sanitizing agents. Such agents can take the form of solutions of small molecule bacteriocides, bacteriostatic agents, and others. Alternatively, the sanitizing agents can take the form of polymeric agents that can form sanitizing coatings on the surfaces.

Polymeric compositions containing quaternary ammonium moieties have been used in many sanitizing environments. Quaternary ammonium compound containing polymeric substances have been used in a variety of different forms. A water insoluble reaction product of a quaternary ammonium compound and a carboxylic acid functional polymer composition has been placed in solution in a compatible organic solvent and applied to surfaces to form a film. The prior art also recognizes that such water insoluble reaction products can be formed by contacting, for example, a fabric or an activated carbon particle, first with an aqueous polymer solution and second with an aqueous quaternary ammonium compound solution. In this way the insoluble product forms on the fabric surface or in the activated carbon particle. Alternatively, polymers can be made from monomers containing a quaternary ammonium moiety. For example, copolymers can be prepared from monomers such as a copolymerizable vinyl benzyl quaternary ammonium salt compound or from a quaternary ammonium salt compound having one or more ethylenically unsaturated groups attached directly to the ammonium nitrogen.

We have found in our developmental work that the insoluble precipitates, formed by reacting a quaternary ammonium compound and a carboxylic acid containing polymers, are difficult to handle in a solid composition or in water based form. Further, the compositions which can be used and applied from organic solvent can be expensive and can be hazardous in view of the toxicity and flammability of certain useful solvents. Lastly, the polymers made from quaternary ammonium containing monomers appear to have reduced sanitizing properties that appear to relate to the reduced solubility of the polymer.

Accordingly a substantial need exists for developing an easily applied sanitizing polymeric film made from a carboxylic acid functional polymer and a quaternary ammonium compound.

BRIEF DESCRIPTION OF THE INVENTION

We have found that a sanitizing, water-insoluble polymeric film can be formed from a two-package sanitizer composition. The two-package composition comprises, in a first package, an aqueous solution of an effective amount of a sanitizing, quaternary ammonium salt compound and, in a second package, a substantially neutralized aqueous solution of an acid functional polymer having pendent acid groups such as carboxyl ($-CO_2H$ or salt thereof), sulfonic acid ($-SO_3H$ or salt thereof), or phosphonic acid ($-PO_3H$ of salt thereof). The quaternary ammonium compound and the carboxylic acid polymer composition remain soluble in the two packages while separated but can be cosprayed onto an application surface. Cospraying the two-package composition onto an application surface results in a surface reaction resulting in the formation of the insoluble sanitizing film in situ. One aspect of the invention involves using a single spray head in which the two-package composition is simultaneously sprayed from separate spray nozzles or spray orifices in the spray head. Alternatively a single head and nozzle can be used in which the two-package solutions are simultaneously contacted in the spray head, mixed and immediately sprayed to form the insoluble coating on the surface.

DETAILED DISCUSSION OF THE INVENTION

The sanitizing films of the invention are prepared by co-spraying an aqueous solution of a quaternary ammonium compound with an aqueous solution of a substantially neutralized carboxylic acid functional polymer.

THE MICROBIOCIDAL QUATERNARY AMMONIUM COMPOUND

The films formed from the two-package sanitizing composition of this invention will incorporate an amount of one or more microbiocidal sanitizing agents effective to both disinfect or sanitize surfaces upon contact and to impart prolonged antimicrobial or sanitizing action to the polymeric films prepared. A wide variety of antimicrobial quaternary ammonium compounds may be included in effective amounts without inducing undesirable interactions or chemical reactions between the major components of the compositions. Preferred quaternary ammonium compounds for use in the invention include the quaternary ammonium salts having the structure $(R)(R_1)(R_2)(R_3)N^+X^-$ wherein R, $R_1$, $R_2$, and $R_3$ are independently selected from groups including benzyl, alkyl benzyl, halo benzyl, $C_{1-4}$ alkyl, $C_{5-24}$ alkyl or $C_{1-4}$ hydroxyl alkyl, and $X^-$ represents an anion capable of imparting water solubility or dispersibility. Such anions include chloride, bromide, iodine, sulfate, methylsulfate, and others.

In somewhat greater detail, R, $R_1$, $R_2$, and $R_3$ can be selected from moieties including alkyl, for example methyl, ethyl, propyl, butyl; substituted alkyl, for example hydroxyethyl, hydroxypropyl; cycloalkyl, for example cyclohexyl; aryl, including phenyl, naphthyl, etc.; aralkyl, for example benzyl, substituted benzyl, etc.; alkaryl, for example tolyl, xylyl, alkylnaphthyl; $C_{6-24}$ higher alkyl including hexyl, 2-ethylhexyl, octyl, isooctyl, pentyl, dodecyl, tetradecyl, icocyl, etc.

Preferred quaternary ammonium compounds for use in the two-package sanitizing compositions of the invention include a $C_{6-24}$ alkyl dimethylbenzyl ammonium chloride and dimethyl dichlorobenzyl ammonium chloride.

The sanitizing compositions of the invention can additionally include germicidal agents which aid in sanitizing activity of the quaternary ammonium compound. Such germicidal agents include chlorhexidene, chlorhexidene gluconate, glutaral, halozone, hexachlorophene, nitrofurazone, nitromersol, providone, iodine, thimerosol, $C_{1-5}$ parabens, hypochlorite salts, phenolics, metabrome silan, glycerol laurate, pyrithrone compounds, etc.

ACID FUNCTIONAL POLYMER

The water insoluble sanitizing films of the invention are formed in a reaction between a quaternary ammonium compound and an acid functional polymer. By acid functional polymer we mean a polymer with a pendent acid group such as a pendent carboxyl group, a pendent sulfonic acid group or other acid groups.

Preferred acid functional polymers are typically polymeric compositions having pendent carboxyl groups that can be water soluble, partly soluble or insoluble. The polymers are soluble when neutralized by a basic reactant. Water solutions of the substantially neutralized carboxylic acid polymer are prepared and are co-reacted with the quaternary ammonium compound to form the insoluble films of the invention.

We have found that the preferred water insoluble sanitizing films can be made from (i) a homopolymer polymer made from an ethylenically unsaturated carboxylic acid containing monomer and (ii) a copolymer made from a monomer mixture containing an ethylenically unsaturated carboxylic acid containing monomer or a mixture of homopolymers and/or copolymers.

Alternatively, the water insoluble sanitizing films of the invention can be made by reacting quaternary ammonium compound with a polymer having pendent acid groups other than a carboxyl. Such pendent groups can include sulfonic acid groups, phosphonic acid groups, etc. Such polymers can be made by forming homopolymers or copolymers by polymerizing a mixture of monomers containing monomers having sulfonic acid groups, phosphonic groups, etc. Examples of monomers having pendent sulfonic acid groups include vinyl benzene sulfonic acid, acrylamidoalkyl sulfonic acid, ethylenically unsaturated olefin sulfonic acid, and others well known to the skilled artisan.

Suitable examples of ethylenically unsaturated phosphonic acid compounds for use in the invention are shown in the following formula:

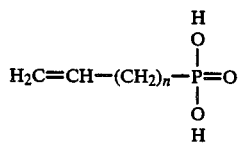

wherein n is an integer of 1-12.

The acid functional polymer preferably can be a homopolymer or copolymer containing an ethylenically unsaturated carboxylic acid containing monomer. Such ethylenically unsaturated carboxylic acid containing monomers include methacrylic acid, acrylic acid, itaconic acid, aconitic acid, cinnamic acids, crotonic acids, mesaconic acids, carboxyethyl acrylic acid, maleic acid, fumaric acid, etc. The carboxylic acid functional copolymer can contain other ethylenically unsaturated monomers compatible with the ethylenically unsaturated carboxylic acid containing monomers disclosed above. Such monomers include ethylene (ethene), propylene (propene), isobutylene, vinyl chloride, vinyl acetate, styrene, chlorostyrene, and others well known to the polymer chemist. Further, the polymers can contain hydrophilic ethylenically unsaturated monomers having amino groups, hydroxyl groups, ether groups, ester groups, and others. Preferred carboxylic acid functional polymers are homopolymers of acrylic acid or methacrylic acid or copolymers containing acrylic acid or methacrylic acid and a second carboxylic acid containing monomer selected from the group consisting of itaconic acid, maleic acid or anhydride wherein in the copolymer the molar ratio between the acrylic monomer and the second monomer is about 1-5 moles of acrylic monomer per each mole of second monomer.

Alternatively the carboxylic acid functional polymer can be a polysaccharide having pendent carboxylic acid groups. Examples of such polysaccharide carboxylic acid functional polymers include (1) carboxyalkyl cellulose such as carboxymethyl cellulose and carboxyethyl cellulose, (2) carboxyalkyl starch such as carboxymethyl starch and carboxyalkyl starch, (3) alginic acid and alginic acid derivatives, (4) pectic (pectinic acid) or (5) similar natural and synthetic carboxylic acid derivatives of a polysaccharide. One form of the carboxylic acid containing polysaccharide compounds comprises a derivative of cellulose which is a polymer comprising monomers derived from $C_6$ saccharide monomers. Typically cellulose is linked with beta (1→4) linkages. Carboxylate cellulose compositions can be prepared by treating cellulose with caustic soda to convert the hydroxyl groups to a sodium cellulosate intermediate. Such product is then reacted with a monochloro carboxylic acid reactant to convert the sodium containing groups to form a carboxylate polysaccharide compound. Similarly, starch and other polysaccharide compositions can be treated to introduce carboxyl groups. Alternatively, alginic acid and pectic (or pectinic) acid are natural products having carbohydrate (polysaccharide) type structures containing paranose units each having a single naturally occurring carboxyl ($CO_2H$) group bonded to a carbon on the ring of the polysaccharide monomer. Preferred alginic acid is derived from Pacific kelp and is converted to commercially useful sodium salts by known reactions. Pectic acid is derived from fruit products and can be conventionally converted into the sodium salt as a reactant for preparing the sanitizing films of the invention.

Either of the aqueous solutions comprising the two-package film-forming compositions of the invention can contain additional compositions that can improve the ease of use, film properties, and usability of the two-package system. Such agents include perfumes, dyes, anti-foam agents, leveling agents, plasticizers, humectants, and other known functional additives.

The film-forming polymers and copolymers of the invention can be prepared by polymerizing the monomers in a solvent or solvent mixture at conventional polymerization concentrations. Preferred solvents include lower alkanols, ketones, glycol esters, etc. The solvent should be selected keeping in mind that the compositions will be used in a sanitizing environment in hospitals and food preparation areas. The polymerization reactions are initiated in the conventional manner using typically radical forming initiators such as dibenzoyl peroxide, tertiary butyl peroctoate, cumene hydroperoxide, diazodiisobutyrodinitrile, ammonium persulfate, and others including combinations thereof.

The two-package compositions of this invention comprise aqueous solutions of the reactants maintained in separate solutions. Typically the two-package solutions are maintained at approximately stoichiometric amounts such that little unreacted quaternary ammonium compound or carboxylic acid containing polymer remain after the reaction. Typically the concentration of the active ingredients in each aqueous solution ranges from about 0.1 to about 30 wt-%, preferably about 0.5–15 wt-%, and most preferably for reasons of rapid reaction, economy, and performance, about 0.75–10 wt-%.

The two-package film-forming sanitizing compositions of the invention are readily prepared by dissolving the quaternary ammonium compound or the neutralized carboxylic acid containing polymer in aqueous solution in separate preparation vessels. The aqueous compositions can contain the additional ingredients useful in the two-package sanitizer which can be added at any stage in the preparation of the two-package sanitizer composition. The carboxylic acid containing package is typically made by neutralizing the carboxylic acid containing polymer in its package or by preneutralizing the polymer prior to preparation. The two-package sanitizer composition takes the form of homogeneous liquids which can be applied to surfaces by spraying, brushing, coating, pad coating, or similar procedures which apply a measured amount of each aqueous package uniformly to the surface area. It is important that controlled amounts of each of the two-packages are applied uniformly and that the application area is covered. In view of these application requirements, co-spraying the two-packages provides an accurate, controlled delivery of the two packages to the treatment surface in the correct proportions for proper film formation.

Each package of the two-package sanitizing film-forming compositions of the invention can be applied to a surface in order to form the sanitizing coatings of the invention. The packages can be applied to the surface in amounts such that about 0.01 to about 100 moles of quat is applied to the surface per each mole of carboxylic acid functionality in the polymer. To obtain initial sanitizing capacity, the quaternary ammonium compound can be present in the film-forming surface sanitizer compositions of this invention at an amount in excess of the polymer. Accordingly, the sanitizers of the invention can contain greater than about 1 to 10 moles of quaternary ammonium compound per mole of carboxylic acid functionality in the polymer. Preferably, for reasons of quick sanitization and long lasting film formation, the film-forming compositions of the invention can contain greater than about 1 to about 5 moles of quaternary ammonium compound per mole of carboxylic acid functionality in the polymer.

Operating within the ranges having at least some excess of quaternary ammonium compound, sanitization of the surface can be rapid upon application and the films formed by the application of the sanitizing compositions of the invention can maintain long term sanitizing character of the surface. Even after successive aqueous wipings of the surface of the films of the invention, antimicrobial properties can be significant.

The two-package sanitizing composition can be co-sprayed from a single head having two spray nozzles providing a spray pattern in which the packages are directed to substantially overlapping areas on the application surface. The concentration of the active ingredients in each package and the spray orifices can be adjusted to insure that the co-spray nozzle delivers approximately stoichiometric or other desired molar application ratios of the package to the surface to be treated. Using a single co-spray nozzle provides the benefit of a simultaneous single application of both packages on a surface with the coincidental rapid film formation through reaction between acid and quat functionality. Alternatively the two packages an be applied to a surface using a single spray nozzle having a mixing chamber immediately prior to the spray orifice wherein the two packages are intimately mixed prior to delivery. Spraying and flow rate of the composition are conducted such that little precipitation or other reaction between quat and acid occurs prior to film formation. Such spray nozzles typically have a mixing/baffle chamber providing a mechanical mixing vortex which intimately contacts each package prior to spray delivery.

The reaction rates between the quaternary ammonium compound and the carboxylic acid functional polymer can be selected through choice of ingredients to insure that (1) significant precipitation or other reaction does not occur prior to delivery and (2) the film forms when the combined solutions are applied to the surface.

The sanitizing film-forming compositions of the invention can be used in household, industrial, institutional, sanitizing activities. However, the compositions of the invention are preferred for use in industrial and institutional areas where sanitizing activity is critical and large surface areas exist requiring sanitizing, which areas require the rapid, efficient application of the sanitizing film. The compositions of this invention are particularly suited to sanitize hard surfaces such as piping, ceramic tile, concrete floors and walls, glass and metal equipment surfaces, flexible plastic functional equipment, covers, and wood surfaces.

Generally the coating process is continued to the extent that an amount of the sanitizing film is delivered to the surface to form an integral, uniform polymeric film. The film should contain about $10^{-5}$ to 1.0 milligrams, preferably $10^{-2}$ to 1.0 milligrams of the quaternary ammonium complex salt film-forming composition, depending on the molecular weight of the quat, per square centimeter of the surface to be treated. Additional amounts of the film can be added to an applied film in order to provide higher levels of sanitizing at application or to renew film integrity. Further, the films formed in an application can be augmented by additional applications of the sanitizing compositions over time. At such time that the surface requires cleaning or that the surface appears to have lost its sanitizing properties, the films of the invention can be removed by dilute acid such as approximately 0.01 to 5N hydrochloric acid, sulfuric acid, acetic acid, etc.

The invention will be further described by reference to the following detailed Examples which contain a best mode.

The following are examples of coatings that have been tested for microbiological efficacy which contain a best mode. Each Example requires two solutions.

EXAMPLE A

In a 5 liter beaker an aqueous polymer solution was made by diluting with deionized water 183 grams of a 49% active itaconic/acrylic acid (about 2.5:1 mole ratio) copolymer to a total of 3000 grams. The contents of the beaker were stirred and sufficient concentrated ammonium hydroxide was added until the pH was 8.5.

Similarly in a 5 liter beaker a quaternary alkyl dimethyldichlorobenzyl ammonium chloride (alkyl 50% $C_{12}$, 30% $C_{14}$, 17% $C_{16}$, 3% $C_{18}$) ammonium salt solution was prepared by diluting with water 380 grams of a 60% active quaternary ammonium salt to 3000 grams.

EXAMPLE B

In a 5 liter beaker an aqueous polymer solution was made by diluting with deionized water, 122 grams of a 49% active itaconic/acrylic acid (about 2.5:1 mole ratio) copolymer to 2950 grams. The contents of the beaker were stirred and 50 grams of a commercial terpolymer (Alco Exp. 1098-5) were added with stirring and the pH was adjusted to 8.5 with concentrated ammonium hydroxide.

Similarly, in a 5 liter beaker a quaternary (alkyl dimethylbenzyl ammonium chloride (40% $C_{12}$, 50% $C_{14}$, 10% $C_{16}$) ammonium salt solution was prepared by diluting with water 272 grams of a 60% active quaternary ammonium salt to 3000 grams.

Each Example was coated using a Binks Formulator "K" air operated formulator at 75 psi equipped with a Binks Model 43P high pressure airless spray gun. Two passes are made over ceramic tiles. The coating weight of the dried film is approximately 0.5 milligrams per square centimeter for Example A and 0.06 milligrams per square centimeter for Example B.

INITIAL DISINFECTANT SPRAY TEST

Test Procedure Followed

Germicidal spray products as Disinfectants, Official Final Action, Official Methods of Analysis of the Association of Official Analytical Chemists, 4.030–4.032, 14th Edition, 1984.

Organisms Tested

*Staphylococcus aureus:* ATCC 6538
*Salmonella choleraesuis:* ATCC 10708

Results

Expressed as number of negative tubes, tubes showing no growth, per number of tubes tested.

TABLE 1

| Formulation | Staphylococcus aureus | Salmonella choleraesuis |
|---|---|---|
| Example B | 10/10 | 8/10 |
| As above + 10% increase in Quaternary | 10/10 | 8/10 |
| As above + 20% increase in Quaternary | 10/10 | 9/10 |

Controls

Appropriate positive controls and neutralizer efficacy evaluations were performed with proper results obtained.

WATER EXPOSURE TEST PROCEDURE

This test is designed to determine the ability of a surface sanitizer formulation to give reduction of transient microbial contamination when used in sanitizing precleaned nonporous food contact and/or non-food contact surfaces. It is also intended to determine the formulations ability to leave a residual antimicrobial film which can withstand varying amounts of water exposure:

Step 1: Tile Preparation/Treatment

1. Tile surfaces are prepared by spraying a known amount of the test formulation onto precleaned 4"×4" square tiles which may include, but are not limited to the following: glazed and unglazed ceramic, glass, PVC plastic, formica, and stainless steel.

2. Treated tiles are allowed to air dry at room temperature.

3. Treated tiles are then exposed to a distilled water shower spray for a specified amount of time, i.e. 0, 1, 3, 5, 10, 15, 30, and 60 minutes.

Shower spray is provided by a bar containing Telejet TN 1.5 spray nozzles which provided an overlapping spray pattern at a volume of 1.5 gallons/hour.

4. Tiles are immediately removed from the shower at their respective times and allowed to air dry at room temperature in a vertical position for approximately 2 hours prior to the residual antimicrobial efficacy testing.

5. Control surfaces containing all ingredients except the antimicrobials are also prepared as in Step 1 along with a control surface which has no surface treatment.

Step 2: Residual Antimicrobial Efficacy Test Procedure

1. Reagents:
   a. Culture Media—cultures are maintained following ADAC Methods, as specified in Sections 4.001–4.002 and 4.020 of the Official Methods of Analysis of ADAC, 14th Edition (1984).

Cultures are maintained on nutrient agar slants by monthly transfers, except *Ps. aeruginosa* which is carried on Cystine Trypticase agar, as specified in Section 4.001.

From the above stock cultures, tubes of ADAC nutrient broth are inoculated and incubated at 37° C. and 1° C. Broth cultures are transferred daily with incubation at 37° C. Cultures used for these tests are incubated 18–24 hours at 37° C.

b. Subculture Media—use tryptone glucose extract agar.

c. Neutralizer blanks—prepare as described in ADAC Methods 4.020 (c), (d), or other appropriate neutralizer material should be employed.

d. Phosphate buffer dilution blanks—prepare as described in ADAC Methods 4.020 (e), (f).

e. Test organisms—for a non-food contact hard surface sanitizer claim, product must be tested against *Staphylococcus aureus* (ATCC 6538) and *Klebsiella pneumonia,* aberrant (ATCC 4352). *Enterobacter aerogenes* (ATCC 13048) may be substituted for *K. pneumoniae.* For a food contact hard surface sanitizer claim, product must be tested against *staphylococcus aureus* (ATCC 6538) and *Escherichia coli* (ATCC 11229).

2. Resistance of Phenol to Test Cultures: determine resistance to phenol at least every 3 months by ADAC Method 4.001–4.005.

3. Apparatus:
   a. Glassware—sterile bacteriological pipettes. Sterilize at 180° F. in hot air oven ≧2 hours.
   b. Petri dishes—sterile—100×15 mm.
   c. Cotton swatches—sterile 1"×1".
   d. Forceps—sterile.

4. Preparation of culture suspension: from stock cultures inoculate tube of ADAC nutrient broth, ADAC 4.001 A., and make ≧3 consecutive daily transfers (≧30), incubating transfers 20-24 hours at 37° C.+1. Do not use transfer >39 days. If only 1 daily transfer has been missed, no special procedures are required; if 2 daily transfers are missed, repeat with 3 daily transfers.

5. Operating technique:
   a. Treated surface, prepared as above, are inoculated with 1.0 ml of the organism being tested. Inoculum is prepared by adding 11 ml of an 18-24 hour culture, prepared as described in step 1(a), to 99 ml of sterile buffered water and mixed well.
   b. Inoculum is spread evenly over the entire surface using a sterile glass spreader.
   c. Inoculated tiles are allowed to air dry 30 minutes at 37° C.
   d. Initial inoculum is plated using Tryptone glucose extract agar to verify a viable culture and to enumerate the surface inoculum level.
   e. Surviving microorganisms are then recovered by swabbing the entire tile surface with a sterile 1" square cotton swatch which has been wetted with sterile buffered water, approximately 0.5 ml. Cotton swatches are handled aseptically using flamed forceps.
   f. Swabbing of the surface is accomplished by wiping the cloth across the surface using a back and forth motion four times.
   g. Transfer swatch immediately to a sterile tube containing 9.0 ml of appropriate neutralizing broth.
   h. Vortex tubes for approximately 15 seconds and immediately prior to plating for another 5 seconds.
   i. Plate samples, using serial 10-fold dilutions to enumerate surviving organisms. Use tryptone glucose extract agar.
   j. Incubate plates at 37° C. for 48 hours and enumerate.

6. Results: to be considered valid, results must meet standard effectiveness:

For a hard surface sanitizer claim for food contact surfaces, a 99.999% reduction, 5-log reduction, in count of number of organisms when compared to the proper control numbers, is required.

For a hard surface sanitizer claim for non-food contact surfaces, a 99.9% reduction, 3-log reduction, in count of number of organisms when compared to the proper control numbers, is required.

Sterility Controls a. Neutralizer—plate 1 ml from previously unopened tube.
b. Water—plate 1 ml from each type of water used.
c. Media—pour one plate from previously unopened bottle.

TABLE 2

| | Results of the Water Exposure Test (Log Reductions *Staphylococcus aureus* ATCC-6538) | | | | | | | |
|---|---|---|---|---|---|---|---|---|
| | Water Exposure (Minutes) | | | | | | | |
| Formulation | 0 | 1 | 3 | 5 | 10 | 15 | 30 | 60 |
| Example A | >6.9 | 5.6 | 6.1 | 5.9 | 5.8 | 5.0 | 6.3 | 5.5 |
| Example B | >6.5 | 4.0 | 4.6 | 4.8 | 4.3 | 4.2 | 4.5 | 3.6 |

The above specification, Examples and data provide a complete description of the manufacture and use of the two-package sanitizing composition of the invention. Since many embodiments of the invention can be made without departing from the spirit and scope of the invention, the invention resides in the claims hereinafter appended.

We claim:

1. A method of forming in situ a continuous sanitizing film on a surface, from a cosprayable two-package sanitizer composition, which method comprises the steps of
   (i) forming a finely divided spray containing an antimicrobial quat solution and an acid polymer solution, wherein:
      (a) said quat comprises a 0.01 to 10 wt-% aqueous solution of a quaternary ammonium salt compound; and
      (b) said acid polymer solution comprises a 0.01 to 10 wt-% aqueous solution of a substantially neutralized acid functional polymeric compound; the sanitizing film having a ratio of quaternary ammonium salt to polymeric compound sufficient to effectively sanitize the treatment surface;
   (ii) depositing the spray upon the surface to be sanitized so as to form a sanitizing film; and
   (iii) continuously exposing the film to the environment such that the film can provide prolonged sanitizing properties to the exposed surface.

2. The method of claim 1 wherein the substantially neutralized acid functional polymeric compound comprises an alkali metal or ammonium salt of a polymer of repeating units of an acrylate monomer having the formula:

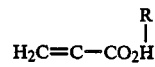

wherein R is hydrogen or $C_{1-12}$ alkyl.

3. The method of claim 2 wherein the polymer additionally comprises repeating units derived from a second monomer comprising an alpha-beta unsaturated dicarboxylic acid compound.

4. The method of claim 3 wherein the alpha-beta unsaturated dicarboxylic acid compound comprises itaconic acid.

5. The method of claim 2 wherein the concentration of quaternary ammonium salt compound is about 0.75 to 2 wt-% and the concentration of the carboxylic acid functional polymeric compound is about 0.75 to 2 wt-%.

6. The method of claim 2 wherein the carboxylic acid functional polymeric compound comprises a copolymer of methacrylic acid and maleic anhydride wherein there are about 3-1 moles of methacrylic acid per mole of maleic anhydride.

7. The method of claim 1 wherein the spray comprises about 1 to 5 moles of quaternary ammonium compound per mole of carboxylic acid functionality on the substantially neutralized acid functional polymeric compound.

8. The method of claim 1 further comprising the step of allowing the spray to dry upon the surface so as to form a film having an outer exposed surface.

9. The method of claim 1 wherein the quat and polymer acid solutions are mixed prior to spraying.

10. The method of claim 1 wherein the quat and the polymer acid solutions are simultaneously sprayed in substantially an overlapping pattern on a surface.

11. The method of claim 1 wherein the quaternary ammonium salt compound comprises a $C_{6-24}$ alkyl dimethylbenzyl ammonium chloride compound.

12. The method of claim 1 wherein the quaternary ammonium salt compound comprises an alkyl dimethyldichlorobenzyl ammonium chloride compound.

13. The method of claim 1 wherein the concentration of quaternary ammonium salt compound is about 0.1 to 5 wt-% and the concentration of the carboxylic acid functional polymeric compound is about 0.1 to 5 wt-%.

14. A method of forming in situ a continuous sanitizing film on a surface, from a cosprayable two-package sanitizer composition, which method comprises the steps of:
  (i) forming a finely divided spray containing both an antimicrobial quat solution and an acid polymer solution, wherein:
    (a) said quat solution comprises a 0.01 to 10 wt-% aqueous solution of a quaternary ammonium salt compound; and
    (b) said acid polymer solution comprises a 0.01 to 10 wt-% aqueous solution of an alkali metal or ammonium salt of a polysaccharide carboxylic acid compound; and
  (ii) depositing the spray upon the surface to be sanitized.

15. The method of claim 14 wherein the polysaccharide carboxylic acid compound comprises an alginic acid compound.

16. A method of forming in situ a continuous sanitizing film on a surface, from a cosprayable two-package sanitizer composition, which method comprises the steps of:
  (i) forming a finely divided spray containing both an antimicrobial quat solution and an acid polymer solution, wherein:
    (a) said quat solution comprises a 0.01 to 10 wt-% aqueous solution of a quaternary ammonium salt compound; and
    (b) said acid polymer solution comprises a 0.01 to 10 wt-% aqueous solution of a derivative of ethylenically unsaturated sulfonic acid or phosphonic acid; and
  (ii) depositing the spray upon the surface to be sanitized.

17. A method of forming in situ a continuous sanitizing film on a surface, from a cosprayable two-package sanitizer composition, which method comprises the steps of:
  (i) forming a finely divided spray containing both an antimicrobial quat solution and an acid polymer solution, wherein:
    (a) said quat solution comprises a 0.01 to 10 wt-% aqueous solution of a quaternary ammonium salt compound; and
    (b) said acid polymer solution comprises a 0.01 to 10 wt-% aqueous solution of a mixture of an acrylic polymer and a polysaccharide carboxylic acid containing polymer; and
  (ii) depositing the spray upon the surface to be sanitized.

18. A method of forming in situ a continuous sanitizing film on a surface, from a cosprayable two-package sanitizer composition, which method comprises the steps of:
  (i) forming a finely divided spray containing both an antimicrobial quat solution and an acid polymer solution, wherein:
    (a) said quat solution comprises a 0.01 to 10 wt-% aqueous solution of a quaternary ammonium salt compound; and
    (b) said acid polymer solution comprises a 0.01 to 10 wt-% aqueous solution of a copolymer of acrylic acid and itaconic acid wherein the polymer contains about 3-1 moles of acrylic acid per mole of itaconic acid; and
  (ii) depositing the spray upon the surface to be sanitized.

19. A method of forming in situ a continuous sanitizing film on a surface, from a cosprayable two-package sanitizer composition, which method comprises the steps of:
  (i) forming a finely divided spray containing both an antimicrobial quat solution and an acid polymer solution, wherein:
    (a) said quat solution comprises a 0.01 to 10 wt-% aqueous solution of a quaternary ammonium salt compound; and
    (b) said acid polymer solution comprises a 0.01 to 10 wt-% aqueous solution of a copolymer of acrylic acid and maleic acid wherein there are about 3-1 moles of acrylic acid per mole of maleic anhydride; and
  (ii) depositing the spray upon the surface to be sanitized.

20. A method of forming in situ a continuous sanitizing film on a surface, from a cosprayable two-package sanitizer composition, which method comprises the steps of:
  (i) forming a finely divided spray containing both an antimicrobial quat solution and an acid polymer solution, wherein:
    (a) said quat solution comprises a 0.01 to 10 wt-% aqueous solution of a quaternary ammonium salt compound; and
    (b) said acid polymer solution comprises a 0.01 to 10 wt-% aqueous solution of a copolymer of methacrylic acid and itaconic acid wherein there are about 3-1 moles of methacrylic acid per mole of itaconic acid; and
  (ii) depositing the spray upon the surface to be sanitized.

* * * * *